United States Patent [19]
Kessler et al.

[11] Patent Number: 6,011,004
[45] Date of Patent: *Jan. 4, 2000

[54] USE OF GROWTH FACTORS TO TREAT DRUG-INDUCTED NEUROPATHY

[75] Inventors: John A. Kessler, New Canaan, Conn.; Stuart C. Apfel, West Hempstead, N.Y.

[73] Assignee: Albert Einstein College of Medicine of Yeshiva University, Bronx, N.Y.

[ * ] Notice: This patent is subject to a terminal disclaimer.

[21] Appl. No.: 08/768,221

[22] Filed: Dec. 17, 1996

Related U.S. Application Data

[63] Continuation of application No. 08/153,796, Nov. 17, 1993, Pat. No. 5,604,202, which is a continuation of application No. 07/612,847, Nov. 13, 1990, abandoned.

[51] Int. Cl.⁷ .................................................. A61K 38/18

[52] U.S. Cl. ................ 514/2; 514/12; 530/350; 530/399

[58] Field of Search ................... 514/12, 21, 2; 530/350, 399

[56] References Cited

PUBLICATIONS

Mollman J.E. 'Cisplatin Neurtoxicity', The New England Journal of Medicine. Jan. 11, 1990; pp. 126–127, 1990.
Peterson et al. 'Never growth Factor Attenuates Nerutoxic Effects of Taxol on Spinal Cord–Ganglion Explants from Fetal Mice', Science, Vol. 217. pp. 377–379, 1987.
Jacowski et al. 'Neural injury repair: hope for the future as barrier to effective CNS regeneration become clearer.' British Journal of Neurosergery. vol. 9, pp. 303–317, 1995.
Database Caplus on STN. No. 10996:540531. Riaz et al. 'Neurotrophic factors in pherperal neuropathes: pharmacological strategies' Prog. Neurobiol. vol. 42, No. 1, pp. 125–143 (Abstract), 1996.

*Primary Examiner*—Cecilia J. Tsang
*Assistant Examiner*—Anish Gupta
*Attorney, Agent, or Firm*—Amster, Rothstein & Ebenstein

[57] ABSTRACT

This invention relates to the use of neuronotrophic factors, such as nerve growth factor (NGF), ciliary derived neuronotrophic factor (CNTF), brain derived neuronotrophic factor (BDNF), neuronotrophin-3 (NT-3), fibroblast growth factor (FGF), epidermal growth factor (EGF), transforming growth factor α (TFG-α), transforming growth factor β (TGF-β) and others to prevent drug-induced neuropathy.

2 Claims, 6 Drawing Sheets

USE OF GROWTH FACTORS TO TREAT DRUG-INDUCTED NEUROPATHY

This application is a continuation of application Ser. No. 08/153,796, filed Nov. 17, 1993, now U.S. Pat. No. 5,604, 202 which is a continuation of application Ser. No. 07/612, 847, filed Nov. 13, 1990 now abandoned.

This invention was made with U.S. Government support the U.S. Government has certain rights in the invention.

FIELD OF THE INVENTION

This invention relates to a method whereby tumors and viruses may be treated without neuropathic side effects. Specifically, it relates to the coadministration of neuronotrophic factors with toxic anti-tumor agents, and neuronotrophic factors with toxic anti-viral agents so that tumors and viruses may be treated, while drug-induced neuropathy is prevented. More generally, the same strategy may be used to prevent neuropathies produced by other classes of drugs.

BACKGROUND OF THE INVENTION

Taxol, cisplatin and vincristine are all promising anti-tumor drugs. Unfortunately, these drugs have the adverse side effects of toxic sensory or sensorimotor neuropathy and neuronal dysfunction. For example, taxol is a plant alkaloid that promotes the assembly of microtubules and stabilizes them. Clinical trials have demonstrated taxol's antineoplastic activity against solid tumors, such as metastatic melanoma. However, taxol causes toxic sensory neuropathy and is cytotoxic to dorsal root ganglion neurons in vitro. When explants of dorsal root ganglion (DRG) attached to the spinal cord are exposed to taxol, unusual arrays of microtubules are formed in neurons and supporting cells, and DRG neurons die. Neuropathies have also resulted when cisplatin or vincristine have been used to treat tumors.

Dideoxycytidine (ddc) and dideoxyinosine (ddI) are anti-viral agents currently being tested in the treatment of AIDS. These agents also have the side effect of toxic neuropathy.

Co-treatment with the neuronotrophic factor, nerve growth factor (NGF), has previously been shown to prevent neuronal death in in vitro experiments (Peterson and Crain, *Science*, 217: 377 (1982)). However, it has been entirely unclear whether the growth factor could preserve normal neuronal function after toxic insults.

The method in the present invention solves the problems of toxic neuropathy and neuronal dysfunction. The method of the present invention involves coadministration of neuronotrophic factors with these anti-tumor and anti-viral agents. Such coadministration results in both the treatment of tumors and viruses, and in the prevention of toxic neuropathy.

SUMMARY OF THE INVENTION

This invention is directed to the coadministration of neuronotrophic factors, such as nerve growth factor (NGF), with toxic anti-tumor agents, such as taxol, cisplatin and vincristine, and anti-viral agents, such as dideoxycytidine (ddc) and dideoxyinosine (ddI), so that tumors and viruses may be treated without the side effect of toxic sensory neuropathy. The principles, strategies, and conclusions are more generally applicable to the prevention of neuropathies produced by other drug categories and for other neuronotrophic factors such as ciliary derived neuronotrophic factor (CNTF), brain derived neuronotrophic factor (BDNF), neuronotrophin-3 (NT3), epidermal growth factor (EGF), fibroblast growth factor (FGF), transforming growth factor α (TGF-α), transforming growth factor β (TGF-β) and others.

for mice treated with cisplatin, cisplatin plus NGF, and a control group of mice treated with the taxol vehicle, cremophor EL.

Figure 6:
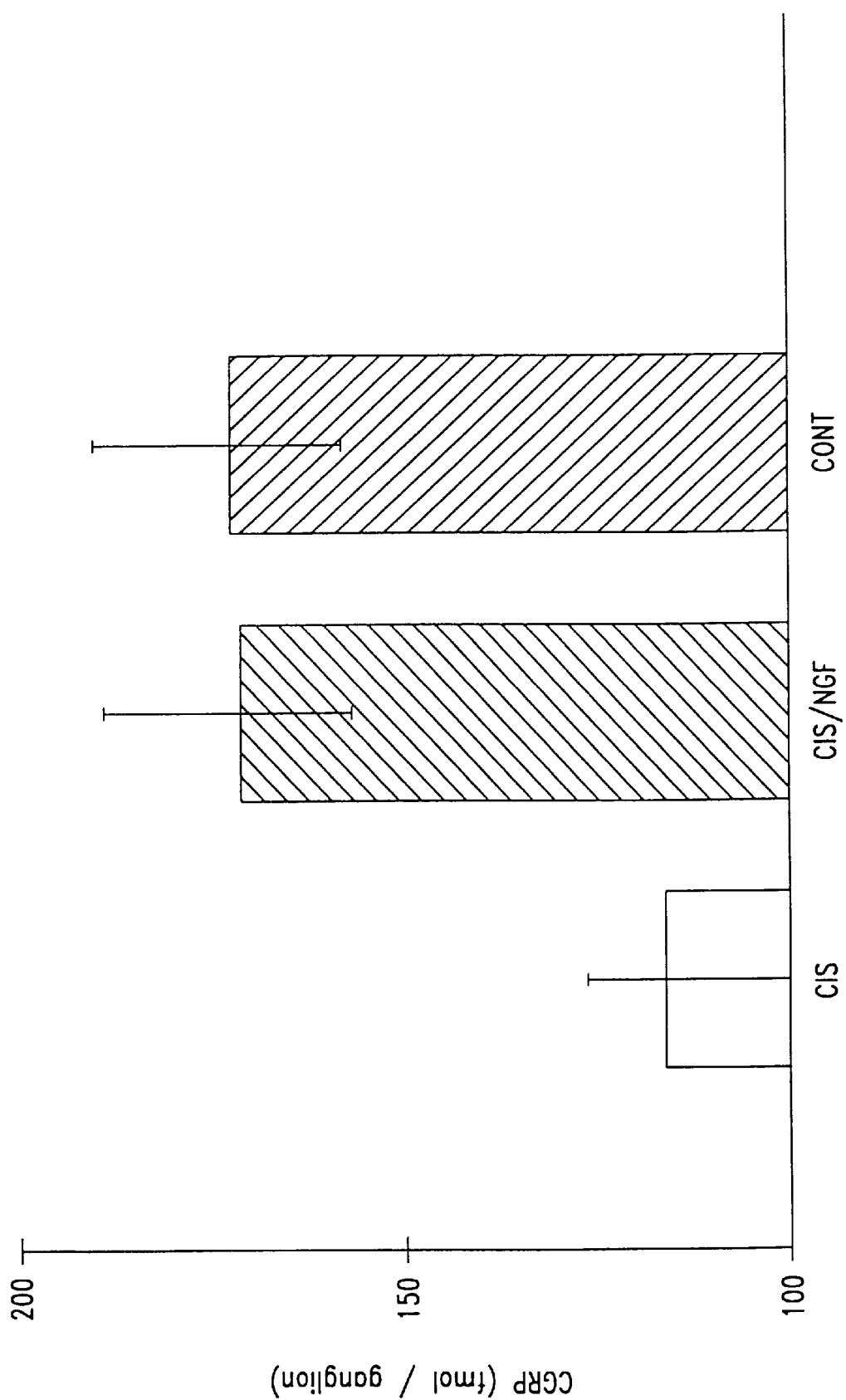

FIG. 6 represents levels of peptide in dorsal root ganglia of mice treated with cisplatin, cisplatin plus NGF, and a control group of mice treated with the taxol vehicle, cremophor EL.

DETAILED DESCRIPTION OF THE INVENTION

Neuronotrophic factors have great promise in the treatment of toxic degenerative disorders of the nervous system in mammals. The method of this invention involves administration to a mammal, preferably a human, of a dose of a neuronotrophic factor that is sufficient to prevent neuropathy induced by any drug. One particularly promising application of neuronotrophic factors, as stated herein, is the prevention of dose limiting toxic neuropathies due to chemotherapeutic (anti-tumor) agents such as, for example, taxol, cisplatin, vincristine, or the like. When administered with taxol or cisplatin, the neuronotrophic factor, nerve growth factor (NGF), prevents toxic sensory neuropathy and prevents taxol and cisplatin from having cytotoxic effects on dorsal root ganglion (DRG) neurons.

Another promising application of neuronotrophic factors is the prevention of dose limiting toxic neuropathies due to administration of anti-viral agents, which include such substances as dideoxycytidine (ddC) and dideoxyinosine (ddI).

Neuronotrophic factors are defined for purposes of this invention as polypeptide factors that enhance neuronal growth and include, for example, nerve growth factor (NGF) (EP 121,338), brain-derived neurotrophic factor (BDNF) (Leibrock, et al., *Nature*, 341: 149 (1989)), ciliary derived neuronotrophic factor (CNTF) (EP 385,060), neuronotrophin-3 (NT3) (Rosenthal, et al., *Neuron*, 4: 767 (1990)), fibroblast growth factor (FGF) (Abraham, et al., *EMBO J.*, 5: 2523–2529 (1986); Jaye, et al., *Science*, 233: 541–544 (1986)), epidermal growth factor (EGF) (EP 128, 733), transforming growth factor α (TGF-α) (U.S. Pat. No. 4,742,003), transforming growth factor β (TGF-β) (U.S. Pat. No. 4,886,747), and other such molecules. The neuronotrophic factor is appropriately from any source, preferably mammalian, and most preferably human. It may be derived from native sources but is preferably made recombinantly. Neuronotrophic factors from animals other than humans, for example porcine or bovine sources, can be used for treating humans.

Neuronotrophic factors such as NGF preserve normal neuronal function. However, the mechanism by which neuronotrophic factors such as NGF prevent taxol and cisplatin neuropathy is unclear. Since NGF regulates the synthesis and stability of some cytoskeletal elements in neurons, it is possible that the growth factor specifically reverses effects of taxol on microtubule assembly. Alternatively, disruption of microtubules may inhibit retrograde neuronal transport of peripherally synthesized NGF, and administration of exogenous growth factor may act by preventing a neuronal growth factor deficiency expected to occur following impaired retrograde transport.

Finally, NGF may stimulate neuronal metabolism in a nonspecific manner, rendering the cell more resistant to toxic insult. Since neuropathy is a dose limiting toxicity of numerous therapeutic agents such as taxol, cisplatin, vincristine, dideoxycytidine, dideoxyinosine and others, coadministration of appropriate neuronotrophic factors such as NGF may limit the toxicity of such drugs. Systematic administration of NGF preserves normal neuron function. This strategy may increase the clinical utility of these and other drugs by making it possible to give higher doses with limited side effects.

In the treatment of cancer patients with growth factors, one must consider the effect of the growth factor on the tumor itself. Some tumors, such as melanoma, have NGF binding sites. However, recent studies demonstrate that not only does NGF not facilitate tumor growth, but it actually inhibits proliferation of malignant cells which have the receptor (Rakowicz-Szulcznyska, et al., *Cancer Res.*, 48: 7200 (1988)). Further, when used as an adjuvant with chemotherapeutic agents, NGF augments the activity of the chemotherapeutic agent in vitro (Goretzki, et al., *Surgery*, 102: 1035 (1987)).

More generally, the beneficial effects of NGF in protecting against neuropathy produced by the widely disparate agents taxol and cisplatin indicate that NGF treatment may be a useful adjunct drug for preventing neuropathy produced by a diversity of chemotherapeutic, antiviral, and other toxic agents.

In the present invention, applicants sought to develop an animal model and then to determine whether NGF can prevent taxol and cisplatin neuropathy in vivo. Administration of taxol and cisplatin to mice resulted in profound sensory neuropathy characterized by elevated threshold to thermally-induced pain, decreases in dorsal root ganglion content of the peptide neurotransmitter, substance P, and diminished amplitude of the compound action potential in the caudal nerve. Coadministration of NGF prevented all of these signs of neurotoxicity. These findings indicate that administration of NGF prevents certain toxic sensory neuropathies.

Therapeutic formulations of neuronotrophic factors are prepared for storage by mixing the factor having the desired degree of purity with physiologically acceptable carriers, excipients or stabilizers (*Remington's Pharmaceutical Sciences*, 16th ed., 1980, Mack Publishing Co., edited by Oslo, et al., the disclosure of which is incorporated herein by reference) in the form of a lyophilized cake or aqueous solutions. Acceptable carriers, excipients and stabilizers are nontoxic to recipients at the dosages and concentrations employed, and include buffers such as phospate, citrate, succinate, acetate, and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine, or lysine; monosaccharides, disaccharides, and other carbohydrates including glucose, mannose, or dextrins; chelating agents such as ethylenediaminetetraacetic acid (EDTA); sugar alcohols such as mannitol or sorbitol; salt-forming counterions such as sodium; and/or nonionic surfactants such as Tween, Pluronics, or polyethylene glycol.

The formulation generally will contain between about 10 and 10,000 $\mu$g/ml of the neuronotrophic factor, depending, e.g., on the condition being treated, the medical history of the patient, and if the neuronotrophic factor is delivered by pump, the pumping rate. The pH of the formulation will be that which is compatible with the body, i.e., in a range of about 4.5 to 7.5, preferably 5 to 7. An example of one formulation is 100 $\mu$g/ml of BDNF of NGF in 10 mM succinate buffer, pH 5, made isotonic with about 120 to 140 mM sodium chloride.

Neuronotrophic factors to be used for in vivo administration must be sterile. This is readily accomplished by filtration through sterile filtration membranes, prior to or following lyophilization and reconstitution. The neuronotrophic factor may be stored in lyophilized form.

Therapeutic neuronotrophic factor compositions may be placed into a container having a sterile access port, for example, an intravenous solution bag, or a vial having a stopper pierceable by a hypodermic injection needle.

The neuronotrophic factor optionally is combined with or administered in concert with another neuronotrophic factor as defined herein and may be coadministered with the drug that causes the neuropathy, i.e., administered in combination with, in concert with, or sequentially with the drug. Such administration includes administering the neuronotrophic factor to the patient prior to administration of the neuropathy-inducing drug.

The route of administration of the neuronotrophic factor is in accord with known methods, e.g., injection or infusion by subcutaneous and parenteral means, including intravenous, intramuscular, intraperitoneal, intracerebral, intrathecal, intranasal and intralesional routes, or by sustained release systems as noted below, most preferably by subcutaneous, intramuscular or intravenous routes.

Suitable examples of sustained-release preparations include semipermeable polymer matrices in the form of shaped articles, e.g., films or microcapsules. Sustained release matrices include polyesters, hydrogels, polylactides (U.S. Pat. No. 3,773,919; EP 58,481), polylactide-polyglycerine copolymers, polyorthoesters, polyacetates, polycaprolactones, copolymers of L-glutamic acid and gamma ethyl-L-glutamate [Sidman, et al., *Biopolymers*, 22 (1): 547–556 (1983)], poly (2-hydroxyethyl-methacrylate) [Langer, et al., *J. Biomed. Mater. Res.*, 15: 167–277 (1981); Langer, *Chem. Tech.*, 12: 98–105 (1982)], ethylene vinyl acetate [Langer, et al., supra], or poly-D-(-)-3-hydroxybutyric acid [EP 133,988A].

Sustained-release neuronotrophic factor compositions also include liposomally entrapped neuronotrophic factors. Liposomes containing neuronotrophic factors are prepared by methods known per se: DE 3,218,121A; Epstein, et al., *Proc. Natl. Acad. Sci. USA*, 82: 3688–3692 (1985); Hwang, et al., *Proc. Natl. Acad. Sci.* USA, 77: 4030–4034 (1980); EP 52,322A; EP 36,676A; EP 88,046A; EP 143,949A; EP 142,641A; Japanese Patent Application No. 83-118008; U.S. Pat. Nos. 4,485,045 and 4,544,545; and EP 102,324A. Ordinarily, the liposomes are of the small (about 200–800 Angstroms) unilamelar type in which the lipid content is greater than about 30 mol. % cholesterol, the selected proportion being adjusted for the optimal neuronotrophic factor therapy.

An effective amount of the neuronotrophic factor to be employed therapeutically will depend, for example, upon the therapeutic objectives, the route of administration, the type of drug being administered, whether the drug is administered simultaneously, and the condition of the patient. Accordingly, it will be necessary for the therapist to titer the dosage and modify the route of administration as required to obtain the optimal therapeutic effect. A typical daily dosage might range from about 1 µg/kg to up to 100 mg/kg or more, depending on the factors mentioned above. Typically, the clinician will administer the neuronotrophic factor until a dosage is reached that prevents the neuropathy induced by the drug. The progress of this therapy is easily monitored by conventional assays such as behavioral (subjective) assays and electrodiagnostic assays involving nerve conduction studies and electromyography wherein the threshold stimulation to the nerve, speed to the brain, and amplitude once in the brain are measured.

The following examples are offered by way of illustration and not by way of limitation. All literature references cited in the example section are expressly incorporated herein by reference.

EXAMPLES

Taxol Tests

It was necessary to first establish an animal model for taxol neuropathy, and to define biochemical, behavioral and electrophysiological parameters of dorsal root ganglion neuron dysfunction. Human taxol neuropathy is characterized by paresthesias, dysesthesias and frequently pain; consequently, applicants chose the tail-flick test to assess the integrity of peripheral nociceptive pathways. The peptide neurotransmitter, substance P, was chosen as a biochemical index since alterations in ganglion neuron function are reflected by changes in peptide content. Human taxol neuropathy is generally associated with slowed nerve conduction; therefore, compound sensory amplitudes and nerve conduction velocities in the tail nerves were measured.

1. The Tail-Flick Tests—Groups of six male CD1 Swiss Albino mice weighing 10–12 gm each were injected daily with 21.6 mg/kg of taxol intraperitoneally for six consecutive days. Equal numbers of mice were injected with the taxol vehicle, cremophor EL, at equal volumes proportionate to weight, to serve as controls. A third group was injected with taxol and 10 ug/gm NGF (prepared from mouse salivary gland using the method of Mobley et al described in Biochem., 15: 5543 (1983), which is incorporated herein by reference) with the NGF injections beginning one day prior to the taxol injections and continuing for seven consecutive days. Three days after the final injection the animals were assessed for thermal pain thresholds using minor modifications of the standard tail-flick test. The tester was blinded to the identity of the animals. Animals were partially restrained, allowing their tails to move freely over a beaker of water which was being heated at a rate of 2° C. per minute beginning at 35° C. The tails were placed in the water to a point 3–4 mm from the tip. The temperature of the water was continuously monitored and recorded at the point the animal flicked its tail out of the water. Results are expressed as mean tail-flick temperature (°C.)±S.E.M.

Figure 1:
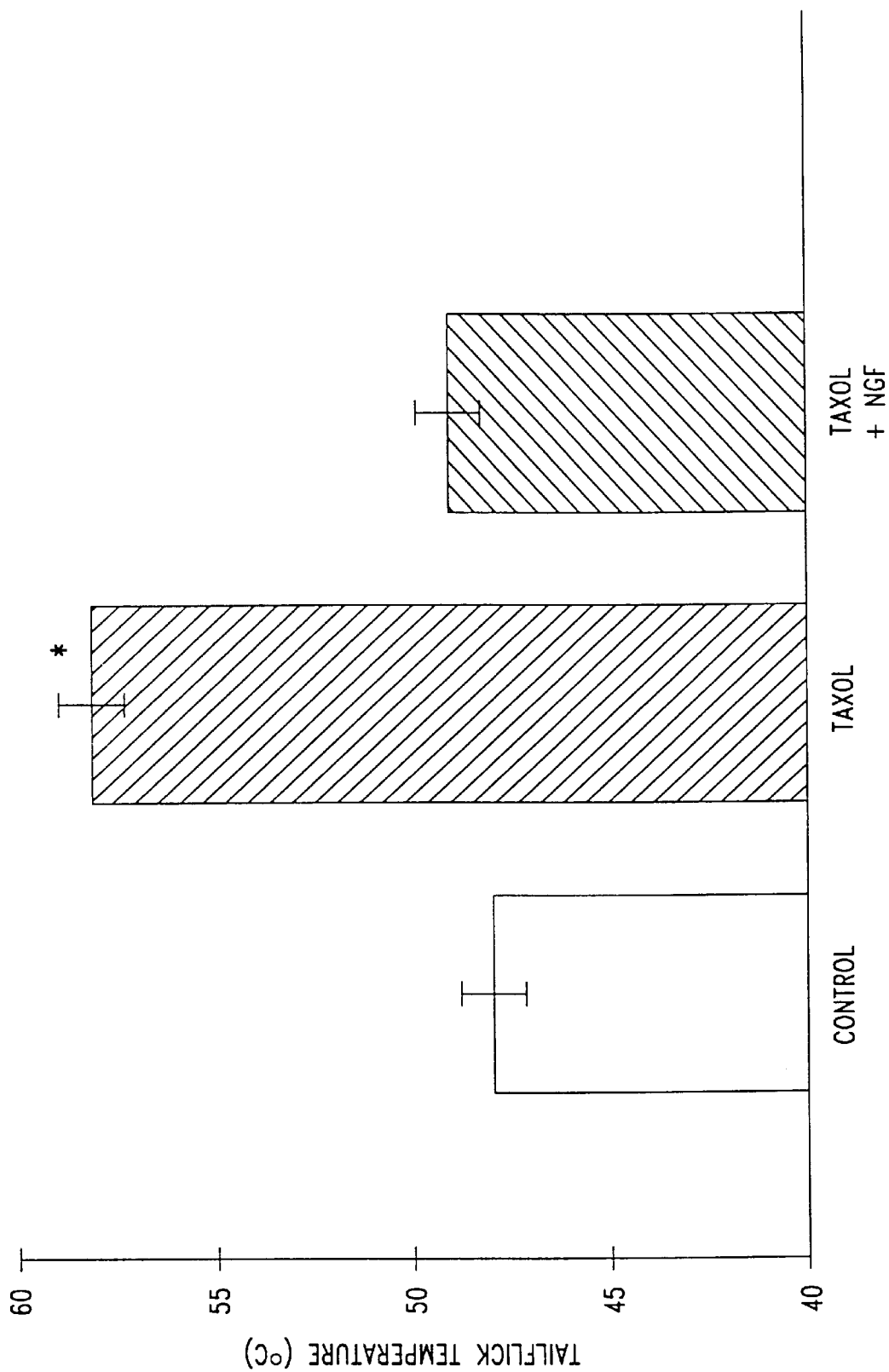
FIG. 1 represents responses to the tail-flick test for mice treated with taxol, taxol plus NGF, and a control group of mice treated with the taxol vehicle, cremophor EL.

2. The Tail-Flick Test Results—The response was elicited in control animals at a mean temperature of 48.1° C. Administration of taxol significantly ($p<0.001$ by Anova) elevated the mean tail-flick threshold to 58.2° C. Two of six animals in the group depicted in FIG. 1 failed to withdraw the tail even at 60° C., at which temperature the test was terminated to prevent undue tissue injury. These two animals also had the lowest ganglion peptide levels. The mean tail-flick threshold in animals treated with both taxol and NGF (49.1° C.) did not differ significantly from controls. Thus, concurrent administration of NGF completely prevented the effects of taxol on this behavioral parameter of sensory neuropathy (see FIG. 1).

3. The Peptide Neurotransmitter Tests—After measurements of thermal sensory thresholds, the animals were sacrificed and both $C_6$ DRG were carefully dissected from each animal. Cervical ganglia were examined rather than lumbosacral ganglia to avoid possible alterations in substance P levels due to thermal stimulation during the tail-flick test and to correlate with our earlier studies of peptide regulation in DRGs. The DRGs were placed immediately into 0.01N HCl, boiled for five minutes, then placed on ice. The tissue was homogenized and processed for substance P (SP) radioimmunoassay using our previously published techniques. Our SP assay can reliably detect 1 pg of peptide. Results are expressed as mean pg per ganglion±S.E.M.

Figure 2:
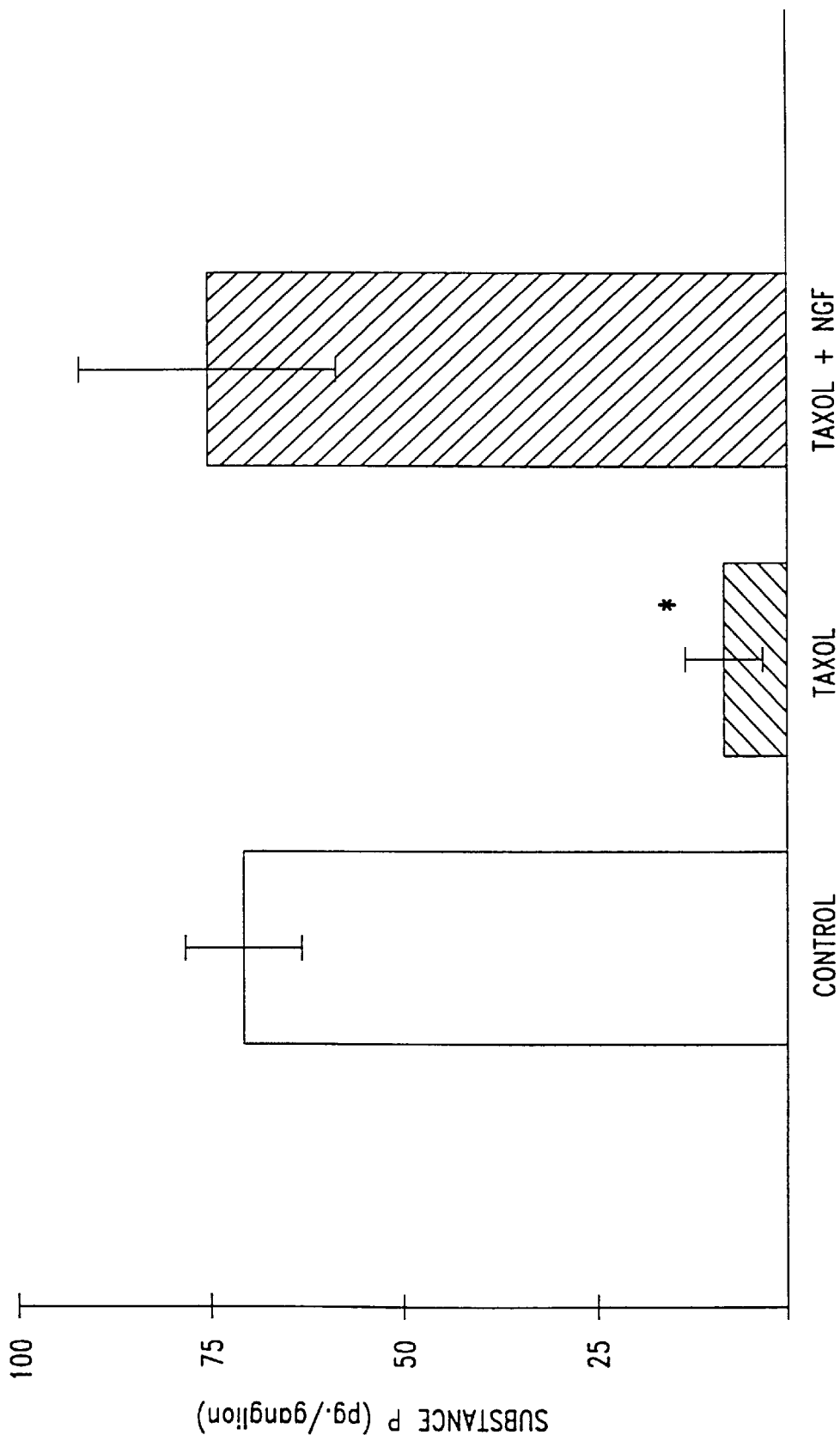
FIG. 2 represents levels of peptide in dorsal root ganglia of mice treated with taxol, taxol plus NGF, and a group of control mice treated with the taxol vehicle, cremophor EL.

4. The Peptide Neurotransmitter Test Results—Injection of taxol significantly reduced ($p<0.001$ by Anova) mean levels of SP in the DRG to 8 pg per ganglion, an 88% reduction compared to the control level of 67 pg/ganglion. By contrast, levels of SP in animals treated concurrently with both taxol and NGF (mean of 73 pg/ganglion) were unchanged compared to control levels. Thus concurrent administration of NGF completely prevented the effects of taxol on ganglion peptide levels (see FIG. 2).

Figure 3:
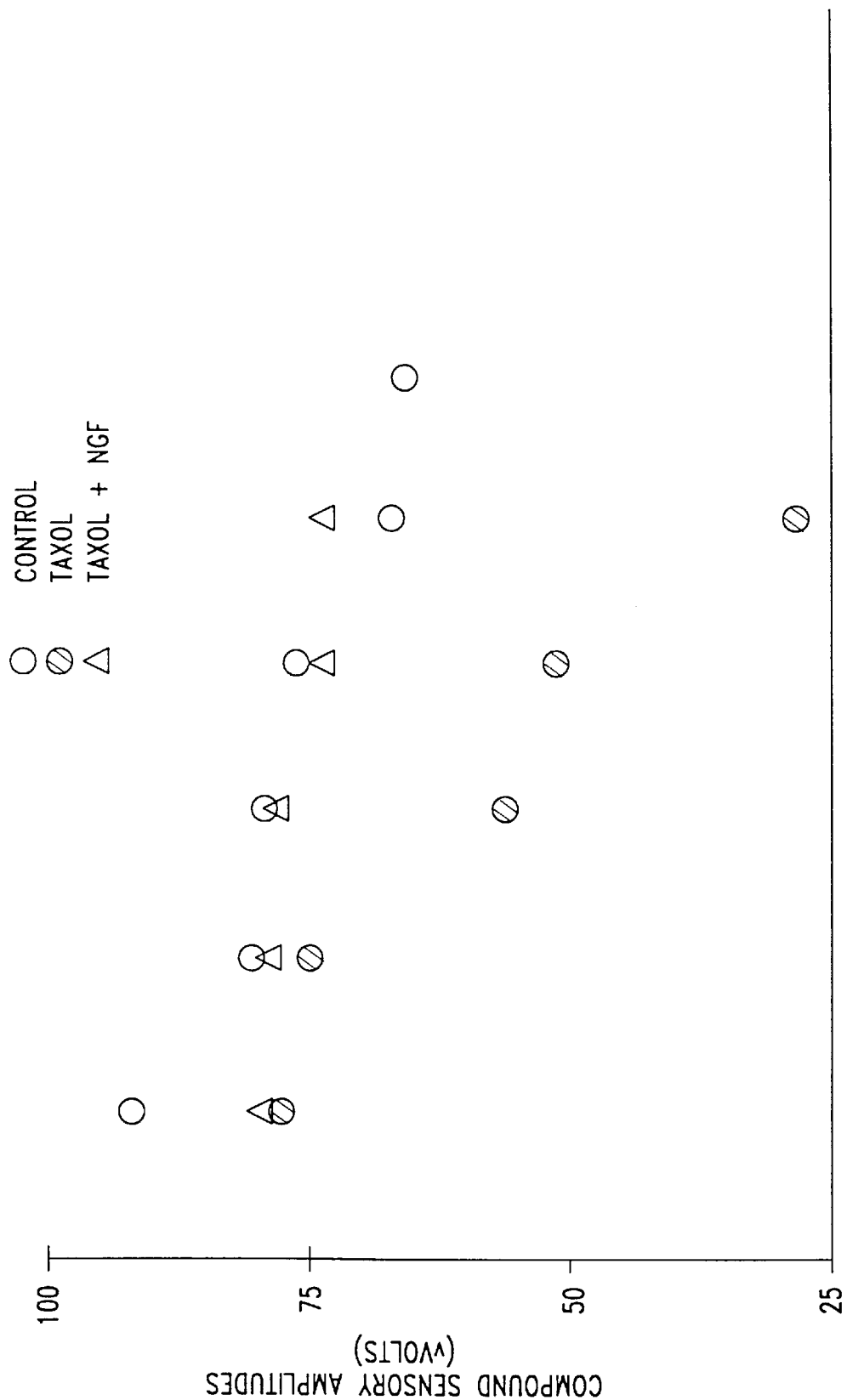
FIG. 3 is a scatter plot of compound sensory amplitudes measured in mice treated with taxol, taxol plus NGF, and a group of control mice.
Figure 4:
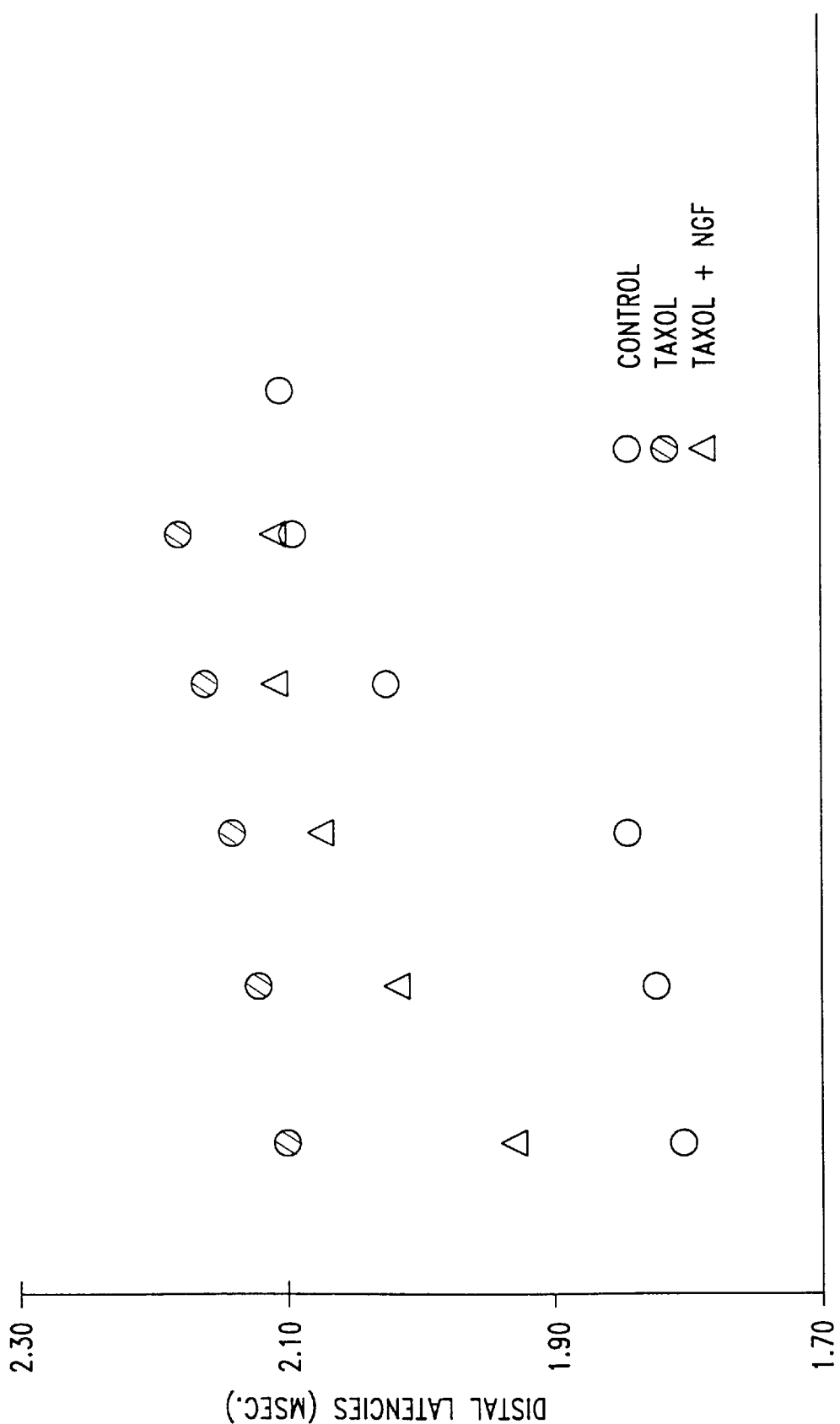
FIG. 4 is a scatter plot of distal latency measured in mice treated with taxol, taxol plus NGF and a control group of mice.

5. The Compound Sensory Amplitude and Nerve Conduction Tests—Electrophysiological testing was done on a different set of mice treated identically to the set described in FIG. 1. Compound sensory amplitudes and nerve conduction velocities were measured in a different group of mice out of concern that some of the mice may have injured their tail nerves during tail-flick testing. The animals were anesthetized with 0.8 mg pentobarbital per 10 gm body weight prior to recording. Platinum-iridium surface electrodes were placed along the distal section of the caudal nerve and the active recording electrode was positioned at a fixed distance of 40 mm distal to the stimulating cathode. Brief pulses of constant voltage stimulation were delivered through an anode-cathode pair positioned overlying a proximal section of the caudal nerve. Ten stimuli were averaged, and then the procedure was repeated. FIG. 3 is a scatter plot of the compound sensory amplitudes ($\mu$ volts) measured in taxol treated, control and taxol plus NGF treated animals. Each point represents the mean value of the two measures for a single animal. Amplitude was measured from baseline to peak to the nearest $0.1\mu$ volts. FIG. 4 is a scatter plot of the distal latency (msec) measured in each animal. Latency was determined from the onset of the initial depolarization and measured to the nearest 0.1 msec.

6. The Compound Sensory Amplitude and Nerve Conduction Test Results—Compound sensory amplitudes are an electrical measurement that measures the height of the action potential that propagates down the axon. An abnormal amplitude implies something is wrong with the axon of the neuron itself. Treatment with taxol reduced the compound sensory amplitudes by 25% from a mean of 77.6 to a mean of $58.6\mu$ volts ($p<0.05$ by Students t test). There was moderate variability in controls and some overlap between groups. This suggests that electrophysiology is less sensitive for detecting this type of neurotoxic injury than measuring peptide levels and thermal pain sensation. Coadministration of NGF with taxol (77.3μ volts; 99.6% of control) completely prevented the decrease in compound sensory amplitude. (See FIG. 3.)

Distal latency is an electrical measurement of the speed with which the action potential signal is carried down the axon. An abnormally prolonged distal latency implies there is something wrong with the myelin sheath (derived from the Schwann cell) that surrounds the axon, and not necessarily the axon itself. Treatment with taxol slightly increased conduction latency from a control mean value of 1.95±0.14 to 2.16±0.06 msec. Coadministration of NGF (2.03±0.09 msec) did not prevent this insignificant prolongation in latency. This change presumably reflected, at least in part, taxol effects on Schwann cells, which do not respond to NGF administration. (See FIG. 4.)

Cisplatin Tests

1. The Tests—Two groups of six CD1 male mice, initially weighing between 10 and 15 grams each, were injected intraperitoneally with cisplatin (Sigma) at a dose of 10 mg/kg diluted in normal saline, on a weekly basis for a total of six weeks. One of these groups also received human recombinant NGF (EP 121,338) injected subcutaneously at a dose of 5 μg/gm mouse three times a week for the same six-week period. The other group of six mice received normal saline injections according to the same schedule as the NGF injections, and the same volume per weight. A third group of age and weight matched male mice were treated once a week with intraperitoneal injections of saline to match the cisplatin injections. This group served as controls.

One week after the final cisplatin injection the mice were tested for thermal sensation using the tail-flick test, and for proprioception using the dowel test. They also underwent electrophysiological testing for distal latency. The animals were then sacrificed, their cervical DRGs were removed and assayed for calcitonin gene related peptide (CGRP) using radioimmunoassay.

Figure 5:
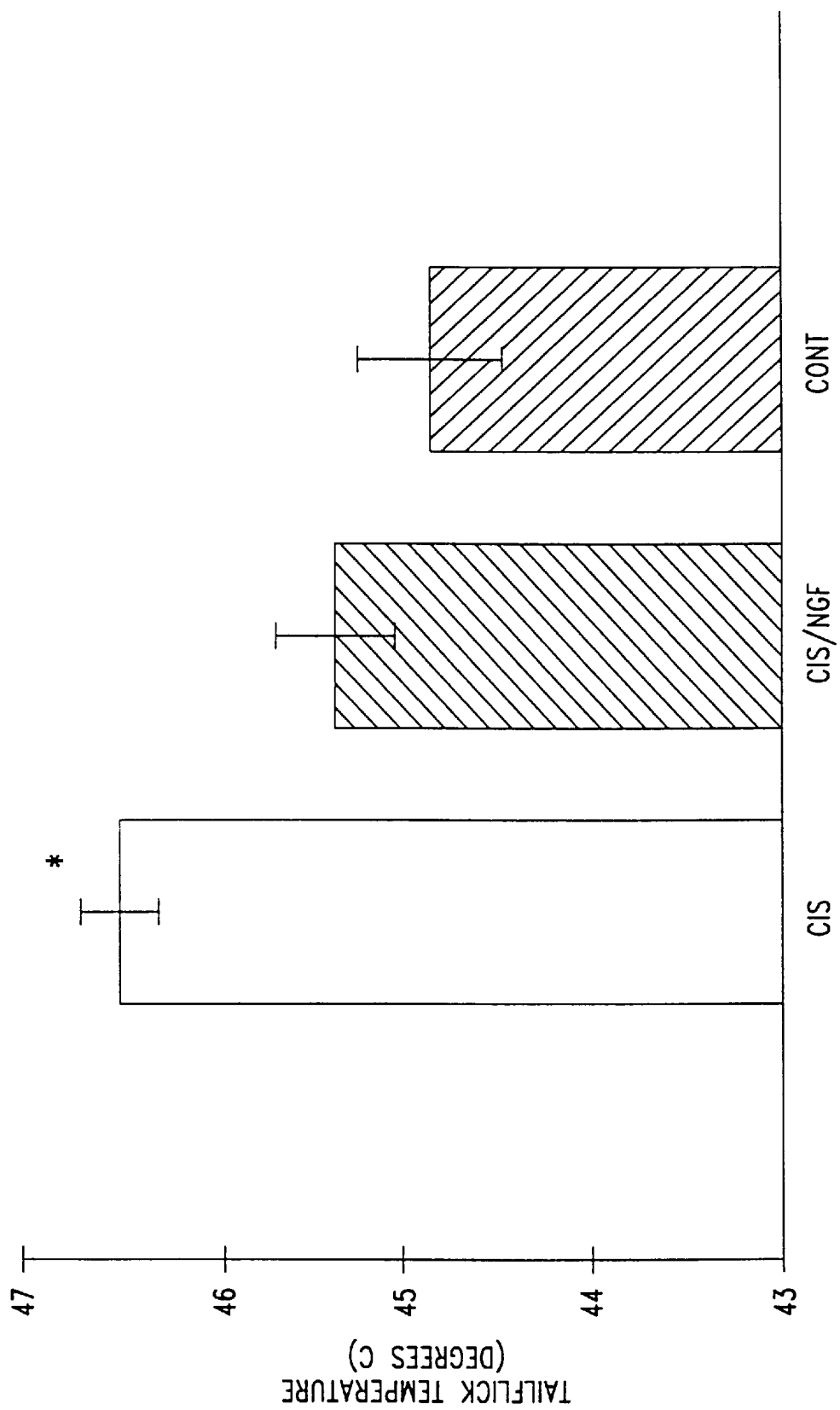
FIG. 5 represents responses to the tail-flick test.

2. The Tail-Flick Test Results—On tail-flick testing, the control group had a mean temperature threshold of 44.8° C. with a standard error of 0.37. The cisplatin group had a mean threshold of 46.4° C. with a standard error of 0.2. The cisplatin plus NGF group had a mean of 45.3° C. with a standard error of 0.33. The cisplatin group differed significantly from the control group with a P value of 0.003 by two-tailed probability. The cisplatin group differed significantly from the cisplatin plus NGF group with a P value of 0.02 by two-tailed probability (see FIG. 5).

3. The Dowel Test Results—For this test, the animals were placed on a dowel 1 cm in diameter, which turned, at a rate of 12 revolutions per minute in the dark. The time was recorded until the animals fell off the dowel, up to a maximum of 15 seconds. The control animals were able to balance themselves for a mean time of 13.6 seconds. The cisplatin treated animals had a mean time of 8 seconds. The cisplatin plus NGF treated animals had a mean time of 12.4 seconds. The cisplatin group differed from the control group significantly with a p valve of 0.003 by two tailed probability. There was no significant difference between the control group and the cisplatin plus NGF group.

4. The Electrophysiological Test Results—The techniques used here were identical to those described for the taxol treated animals. The mean distal latency measured for the control group was 1.63+/−0.04 msec. Animals treated with cisplatin had a significantly prolonged mean distal latency of 1.77+/−0.03 msec. NGF administration prevented the prolongation with a mean latency of 1.67+/−0.4 msec.

5. The Peptide Test Results—The animals were sacrificed following sensory testing and cervical DRGs were removed and processed for CGRP radioimmunoassay. The cisplatin group had a mean CGRP level of 116.2 fmol per ganglion with a standard error of 16.3. The control group had a mean of 172.8 with a standard error of 22.6. The cisplatin plus NGF group had a mean CGRP level of 171.7 with a standard error of 54.2 (see FIG. 6).

These results support the concept that NGF can prevent cisplatin induced neurotoxicity. The behavioral changes associated with cisplatin administration were significantly prevented by coadministration of NGF. NGF administration also maintained CGRP levels at the control value.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

We claim:

1. A method for treating, toxic sensory neuropathy induced by an antitumor agent in a mammal undergoing treatment with said antitumor agent comprising administering prior to or in combination with said antitumor agent treatment an amount of nerve growth factor (NGF) effective to treat toxic sensory neuropathy induced by said antitumor agent.

2. The method of claim 1, wherein said mammal is human.

* * * * *